United States Patent
Hartvigsen et al.

(10) Patent No.: US 9,162,935 B2
(45) Date of Patent: Oct. 20, 2015

(54) COMPACT FT COMBINED WITH MICRO-FIBROUS SUPPORTED NANO-CATALYST

(71) Applicant: Ceramatec, Inc., Salt Lake City, UT (US)

(72) Inventors: Joseph J. Hartvigsen, Kaysville, UT (US); S. Elangovan, South Jordan, UT (US); Lyman Joseph Frost, Idaho Falls, ID (US)

(73) Assignee: CERAMATEC, INC., Sal Lake City, UT (US)

( * ) Notice: Subject to any disclaimer, the term of this patent is extended or adjusted under 35 U.S.C. 154(b) by 177 days.

(21) Appl. No.: 13/772,080

(22) Filed: Feb. 20, 2013

(65) Prior Publication Data
US 2013/0216445 A1 Aug. 22, 2013

Related U.S. Application Data

(60) Provisional application No. 61/601,103, filed on Feb. 21, 2012.

(51) Int. Cl.
*B01J 19/24* (2006.01)
*B01J 8/06* (2006.01)
(Continued)

(52) U.S. Cl.
CPC .............. *C07C 1/041* (2013.01); *B01J 8/067* (2013.01); *B01J 35/0013* (2013.01); *B01J 35/06* (2013.01);
(Continued)

(58) Field of Classification Search
CPC .............. B01J 8/00; B01J 8/02; B01J 8/0285; B01J 8/06; B01J 8/067; B01J 35/00; B01J 35/0013; B01J 35/02; B01J 35/06; B01J 2208/00; B01J 2208/00008; B01J 2208/00017; B01J 2208/00106; B01J 2208/00168; B01J 2208/00194; B01J 2219/00; B01J 2219/00002; B01J 2219/00018; B01J 2219/0002; B01J 2219/32; B01J 2219/322; B01J 2219/32279; B01J 2231/60; B01J 2231/64; B01J 2231/641; C07C 1/00; C07C 1/02; C07C 1/04; C07C 1/0405; C07C 1/041; C10G 2/30; C10G 2/32; C10G 2/33; C10G 71/00; C10L 2200/04; C10L 2200/0461; C10L 2200/0469; C10L 2200/0492; C10L 2290/00; C10L 2290/42
USPC .......... 422/129, 600, 650, 651, 653, 198, 211, 422/310, 312
See application file for complete search history.

(56) References Cited

U.S. PATENT DOCUMENTS

| | | |
|---|---|---|
| 2,895,508 A | 7/1959 | Drake |
| 3,147,084 A | 9/1964 | Franzen et al. |

(Continued)

FOREIGN PATENT DOCUMENTS

| | | |
|---|---|---|
| FR | 2824755 A1 * | 11/2002 |
| KR | 10-0901736 | 6/2009 |

(Continued)

OTHER PUBLICATIONS

Guettel et al., Reactors for Fischer-Tropsch Synthesis, Feb. 18, 2008, Chem. Eng. Technol., 31, No. 5, 746-754.*

(Continued)

*Primary Examiner* — Natasha Young
(74) *Attorney, Agent, or Firm* — David Fonda (57) ABSTRACT

A Fischer Tropsch ("FT") unit includes at least one FT reactor tube. The FT reactor tube is configured to convert syngas into one or more hydrocarbon products. Inside the tube is a nano-sized catalyst particles dispersed in a micro-fibrous substrate. The FT reactor tube may be positioned within a cooling block that may be made of aluminum or another metal. The cooling block includes an aperture, wherein the FT reactor tube is housed within the aperture. At least one cooling channel is located on the cooling block. The cooling channel houses at least one cooling tube that is designed to dissipate the heat produced by the FT reaction.

11 Claims, 10 Drawing Sheets

(51) Int. Cl.

| | | |
|---|---|---|
| *B01J 35/00* | (2006.01) | |
| *B01J 35/06* | (2006.01) | |
| *C07C 1/04* | (2006.01) | |
| *C10G 2/00* | (2006.01) | |
| *F28F 7/02* | (2006.01) | |
| *F28F 13/00* | (2006.01) | |
| *F28D 7/00* | (2006.01) | |
| *F28F 1/12* | (2006.01) | |
| *B01J 8/00* | (2006.01) | |
| *B01J 8/02* | (2006.01) | |
| *B01J 35/02* | (2006.01) | |
| *C07C 1/00* | (2006.01) | |
| *C07C 1/02* | (2006.01) | |

(52) U.S. Cl.
CPC ............... *C10G 2/33* (2013.01); *F28D 7/0025* (2013.01); *F28F 1/12* (2013.01); *F28F 7/02* (2013.01); *F28F 13/003* (2013.01); *B01J 2208/00194* (2013.01); *B01J 2208/026* (2013.01); *B01J 2219/0002* (2013.01)

(56) References Cited

U.S. PATENT DOCUMENTS

| | | | |
|---|---|---|---|
| 3,612,584 A * | 10/1971 | Taylor | 285/148.13 |
| 3,857,680 A | 12/1974 | Porta et al. | |
| 4,170,082 A * | 10/1979 | Freedman | 446/109 |
| 7,501,012 B2 * | 3/2009 | Tatarchuk et al. | 96/132 |
| 8,069,678 B1 | 12/2011 | Bernert | |
| 2002/0048541 A1 | 4/2002 | Schodel et al. | |
| 2003/0175173 A1 | 9/2003 | Karisson | |
| 2003/0180201 A1 | 9/2003 | Belt et al. | |
| 2004/0192989 A1 | 9/2004 | Espinoza et al. | |
| 2005/0080147 A1 | 4/2005 | Hawthorne et al. | |
| 2007/0003460 A1 | 1/2007 | Matsumoto et al. | |
| 2007/0036697 A1 | 2/2007 | Gutlhuber et al. | |
| 2007/0299148 A1 | 12/2007 | Verbist | |
| 2009/0038155 A1 | 2/2009 | Corry | |
| 2009/0215911 A1 | 8/2009 | Wang et al. | |
| 2009/0220389 A1 | 9/2009 | Onishi et al. | |
| 2009/0269258 A1 | 10/2009 | Yi et al. | |
| 2010/0160463 A1 | 6/2010 | Wang et al. | |
| 2010/0303683 A1 | 12/2010 | Hendrie et al. | |
| 2010/0303684 A1 * | 12/2010 | Hendrie et al. | 422/200 |
| 2010/0307726 A1 * | 12/2010 | Chiu et al. | 165/173 |
| 2010/0324158 A1 | 12/2010 | Bowe et al. | |
| 2011/0160318 A1 | 6/2011 | Bos et al. | |

FOREIGN PATENT DOCUMENTS

| | | |
|---|---|---|
| KR | 10-2011-0037640 | 4/2011 |
| WO | WO-2010130399 | 11/2010 |
| WO | WO 2012/131385 A2 * | 10/2012 |

OTHER PUBLICATIONS

Machine translation of FR 2824755 A1, which was published on Nov. 22, 2002.*

Kim, Dong S., "International Search Report", PCT/US2013/026203, (Jun. 13, 2013),1-3.

Kim, Dong S., "Written Opinion of the International Searching Authority", PCT/US2013/026203, (Jun. 13, 2013),1-4.

Kim, Dong S., "International Search Report", PCT/US2013/026939, (Jun. 29, 2013),1-3.

Kim, Dong S., "Written Opinion of the International Searching Authority", PCT/US2013/026939, (Jun. 29, 2013),1-4.

Kim, Dong S., "International Search Report", PCT/US2013/026721, (Jun. 3, 2013),1-4.

Kim, Dong S., "Written Opinion of the International Searching Authority", PCT/US2013/026721, (Jun. 3, 2013),1-6.

Lee, et al., "Bibliography and English Abstract", KR 10-0901736, (Jun. 9, 2009),1-2.

Lee, et al., "Bibliography and English Abstract", KR 10-2011-0037640, (Apr. 13, 2011),1-2.

Guettel, Robert et al., "Reactors for Fischer-Tropsch Synthesis", *Chemical Engineering & Technology*, 2008, vol. 31, Issue 5, (Apr. 22, 2008),746-754.

Nguyen, Huy T., "Non Final Office Action", U.S. Appl. No. 13/767,604, (May 7, 2014),1-17.

Nguyen, Huy T., "Final Office Action", U.S. Appl. No. 13/767,604, (Oct. 21, 2014),1-15.

Nguyen, Huy T., "Notice of Allowance", U.S. Appl. No. 13/767,604, (Jan. 5, 2015),1-10.

* cited by examiner

COMPACT FT COMBINED WITH MICRO-FIBROUS SUPPORTED NANO-CATALYST

RELATED APPLICATIONS

This application claims the benefit of U.S. Provisional Patent Application Ser. No. 61/601,103 filed Feb. 21, 2012. This prior provisional application is expressly incorporated herein by reference.

TECHNICAL FIELD

The present disclosure relates to devices and methods for more efficiently performing Fischer Tropsch ("FT") processing of a syngas stream. More specifically, the present disclosure relates to a device and method for FT processing with improved catalyst and temperature control for more efficient results.

BACKGROUND

The Fischer Tropsch ("FT") process, which is sometimes called FT synthesis, is a chemical reaction used routinely in oil and gas processing. This process involves the conversion of carbon monoxide and hydrogen gas into a hydrocarbon chain and water. This reaction may be summarized as follows:

$$CO + 2H_2 \rightarrow -CH_2- + H_2O \quad \Delta H = -165 \text{ KJ/mol}$$

Generally, a catalyst is used in this reaction. This FT process usually occurs at high temperatures and high pressures, such as, for example, at pressures of 150-600 psig and temperatures ranging from 200-300° C. (The input stream that is input into the FT reaction vessel is often called synthesis gas or "syngas"). FT technology provides a method for conversion of hydrocarbons from one form (e.g. standard natural gas, biomass) to another form (e.g. kerosene & diesel fuel).

The FT process will generally produce a mixture of liquid and gaseous hydrocarbons (—$CH_2$— molecules). In general, the liquid hydrocarbons (such as octane, hexane) tend to be more valuable than the gaseous products (such as methane, ethane, etc.) because these liquid products may be used in producing kerosene, diesel fuel and other desirable products.

The FT process is highly exothermic (with a $\Delta H = -165$ KJ/mol). If the produced heat is not removed as part of the reaction conditions, the metallic catalyst can be damaged and the products generated will tend to be gases rather than the more valuable liquids and gases. Further, care must be taken to insure that sulfur-containing compounds are not part of the syngas as these chemicals tend to poison the catalysts, thereby causing the reaction to fail.

Accordingly, there is a need in the art for a new device and method for FT processing that is more efficient and will better remove the heat produced during the reaction, thereby ensuring that the more valuable liquids are produced during the process. Such a device and method is disclosed herein.

SUMMARY

The present embodiments involve the use of a catalyst in an FT process. This FT catalyst is dispersed within the tubular structures. More specifically, there is a micro-fibrous substrate and the catalyst is dispersed within this micro-fibrous matrix. In some embodiments, the catalyst may be nickel, cobalt, lanthanum, iron, or other alloys, such as FeCuK, CoRu. Further, some of the catalysts (such as Ni, FeCuK, CoRu, etc.) may be positioned on alumina trilobes or alumina pellets, silica or self supporting as desired. The catalyst support may be promoted with Mn or La or other treatments as is apparent to those skilled in the art. The catalyst particle size may range from 10 µm to 1 mm in a micro-fibrous matrix or 0.5 mm to 5 mm for a conventional packed bed of extrudate or similar forms. Those skilled in the art will appreciate what materials may be used as the micro-fibrous matrix.

The use of this type of micro-fibrous structure breaks up flow and thus promotes a more even distribution of the synthesis gas through the FT synthesis tube. Further, a micro-fibrous structure has been shown to provide increased activity by the better utilization of zinc oxide. In other words, zinc oxide may be often used in FT processes to remove sulfur from the syngas, in order to prevent the sulfur from poisoning the cobalt/iron catalyst. By placing zinc oxide within this micro-fibrous matrix, the zinc oxide may more efficiently remove the sulfur. Additionally, proper selection of the micro-fibrous structure could also promote heat transfer (i.e., use of a metallic material for the removal of heat from the highly exothermic FT process and conveying it to the walls of the unit). Since excess heat promotes growth of undesirable light gaseous hydrocarbons, the inability to properly remove heat has limited the use of previously-known fixed bed FT units.

Additionally, the present embodiments also involve the use of one or more water or oil cooling passages that are incorporated into the same block as the FT process. The cooling passages may be cast, extruded, stamped, or machined into the block and may be of varying size and orientation (e.g., co-flow, counter-flow, serpentine, cross-flow, or combinations of the former). The elimination of one of the sets of metal blocks (e.g., the blocks associated with the cooling tubes) simplifies the assembly and operation of the unit, further shrinking the size.

DETAILED DESCRIPTION

The present embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the methods and cells of the present invention, as represented in the Figures, is not intended to limit the scope of the invention, as claimed, but is merely representative of present embodiments of the invention.

Fischer Tropsch (FT) processing is a method for the production of various hydrocarbons from the input of synthesis gas. It is a surface catalyzed carbon polymerization process that largely produces straight chain hydrocarbons that range from $C_1$ to greater than $C_{100}$. Hydrocarbon products generally follow a distribution called the ASF (Anderson-Schultz-Flory) distribution defined by the chain growth probability factor ("α") that is a strong function of temperature. Maintaining the temperature of the catalyst bed at an even temperature is important since higher bed temperatures tend to favor the formation of more of the gaseous (i.e. less valuable) products while lower temperatures tend to favor production of waxes that are not easily transported by pipeline or directly usable as fuel.

The ASF chain growth probability factor (α) decreases by about 0.004/° C. increase in catalyst temperature. This means that a 15° C. variation in local temperature would mean a 0.06 shift in alpha which has a major impact on the product distribution. For example if the optimal alpha value for a desired liquid product was about 0.85, portions of the reactor 15° C. cooler would have an alpha of 0.91 and make too much wax while portions of the reactor 15° C. hotter would make less liquid and too much gas as product. Accordingly, it is desirable to find systems that will control the temperature along the entire length of the FT reactor, and thus the alpha value, to provide consistent results.

Figure 1:
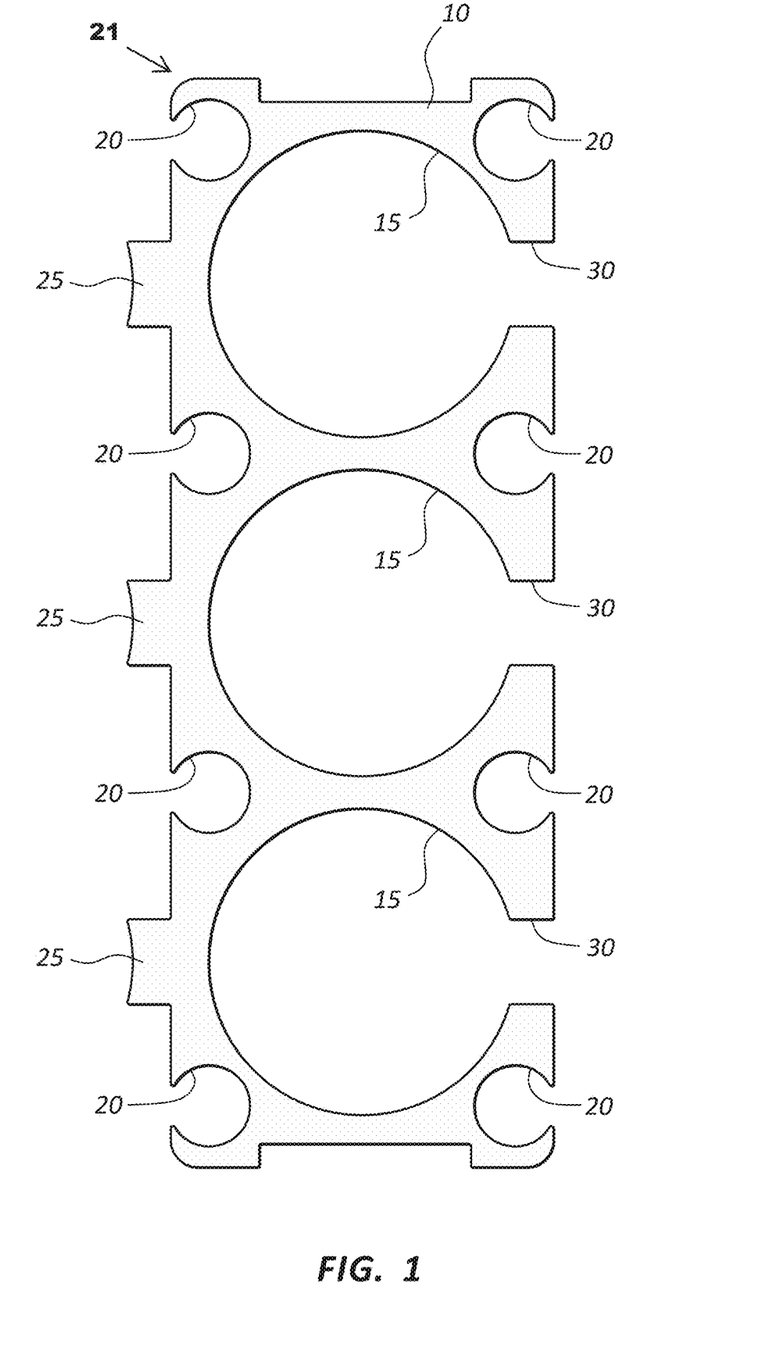
FIG. 1 shows a plan view of a cooling block that may be used in an FT reactor unit.

Referring now to FIG. 1, a plan view for a cooling block 10 that may be used in an FT processing unit is shown. Specifically, the cooling block 10 may be constructed of aluminum or another metal. The purpose of the cooling block is to absorb/dissipate the heat that is produced as part of an FT system.

Specifically, the cooling block 10 comprises at least one aperture 15. As shown in FIG. 1, three (3) apertures 15 are shown. However, other embodiments may have a different number of apertures 15. Each aperture 15 is designed and sized to receive an FT reactor tube (not shown in FIG. 1). More specifically, a metallic (such as carbon steel, copper, brass, stainless steel or aluminum) reactor tube will fit into each aperture 15 so that the FT reaction may occur. The FT reaction occurs within the FT reaction tube. However, as noted above, this reaction is very exothermic and will produce heat. By placing the FT reaction tube within the cooling block 10, the cooling block 10 may absorb/dissipate the heat that is produced during the FT reaction. As described above, if this heat is not dissipated, then the distal end of the FT reactor tube will get hotter (e.g., be at a different temperature) than the proximal end of the FT reactor tube. Such differences in temperature are undesirable as they will cause different portions of the FT reactor tube to have different alpha values, and thus produce different types of liquid/gas products. Accordingly, one of the purposes of the cooling block 10 is to absorb the produced heat, thereby helping to maintain the entire length of the FT reactor tube at the same temperature.

In order to absorb the heat produced by the FT reactor tube, the cooling block 10 may comprise at least one cooling channel 20. As shown in FIG. 1, there are eight (8) cooling channels 20, with four (4) of the channels being positioned proximate the corners 21 of the block 10. However, other embodiments may be designed in which a different numbers of cooling channels 20 are present. (The cooling channels 20 may also be referred to as "cooling passages"). The cooling passages 20 may be cast, extruded, stamped, or machined into the block and may be of varying size and orientation (e.g., co-flow, counter-flow, serpentine, cross-flow, or combinations of the former).

The cooling passages 20 are designed to receive one or more cooling tubes (not shown in FIG. 1). These cooling tubes are metal tubes that will house water, oil or another cooling fluid (not shown in FIG. 1). (A variety of different types of cooling fluids are known in the art and may be used in the present embodiments.) The cooling tubes will absorb the heat that is produced by the FT reactor. In some embodiments, the cooling fluid constantly flows through the cooling tubes, thus absorbing the produced heat and dissipating such heat. Thus, by the use of cooling fluid, the heat produced by the FT reaction may be dissipated and the length of the FT tube may be maintained at substantially the same temperature (and same alpha value).

It should be noted that in some embodiments, the cooling fluid is housed within a separate cooling tube. Those skilled in the art will appreciate that additional embodiments may be designed in which there is no specific tube that houses the cooling fluid; rather the cooling fluid simply flows through the cooling channels 20.

The use of cooling channels 20 that are extruded or otherwise added to the cooling block 10 means that there does not have to be a separate metal block (in addition to the cooling block 20) that houses the cooling tubes. Such elimination of one of the sets of metal blocks simplifies the assembly and operation of the unit, further shrinking the size.

Figure 2:
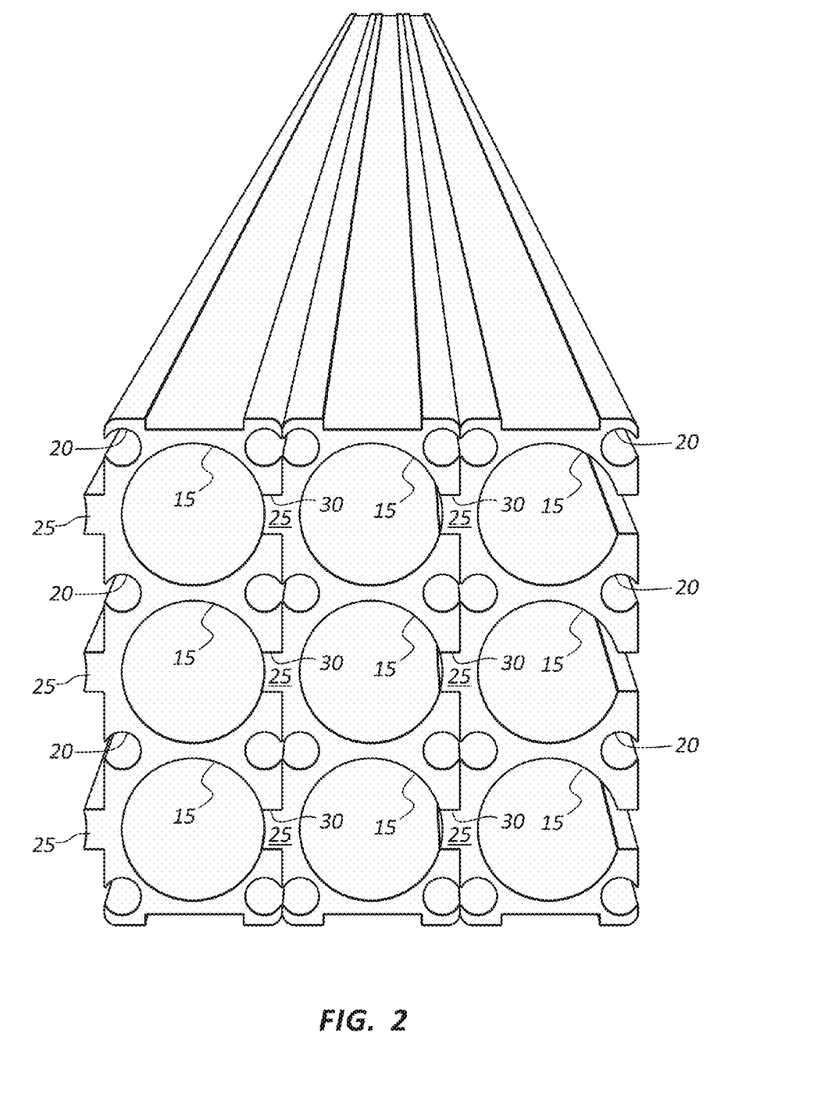
FIG. 2 shows a perspective view of multiple cooling blocks being connected together.

As shown in FIG. 1, the cooling block 10 may further include a male connector extension 25 and a female connector opening 30. The purpose of the male connector extension 25 and the female connector opening 30 is so that adjacent cooling blocks 10 may be connected together (e.g., daisy-chained together). In other words, the male connector extension 25 may interlock with a female connector opening 30 of an adjacent cooling block. Likewise, the female connection opening 30 of the adjacent cooling block may receive the male connector extension 25 of a third block, thereby allowing various cooling blocks to be daisy-chained together. (This connection between the mail connector extension 25 and the female connection opening 30 is shown in FIG. 2.) In this way, the system designer can connect any number of cooling blocks together, as desired.

Referring now to FIG. 2, a perspective view illustrates three (3) cooling blocks 10 being daisy-chained together. Those skilled in the art will appreciate that a different number of cooling blocks 10 may further be connected as desired, in the manner described herein. As can be seen from FIG. 2, when the blocks 10 are positioned together, a three dimensional structure is created. This three-dimensional structure is capable of receiving FT reactor tubes and FT cooling tubes. The longitudinal length of each cooling block 10 depends upon the particular application and the length of the FT reactor tubes.

Figure 3:
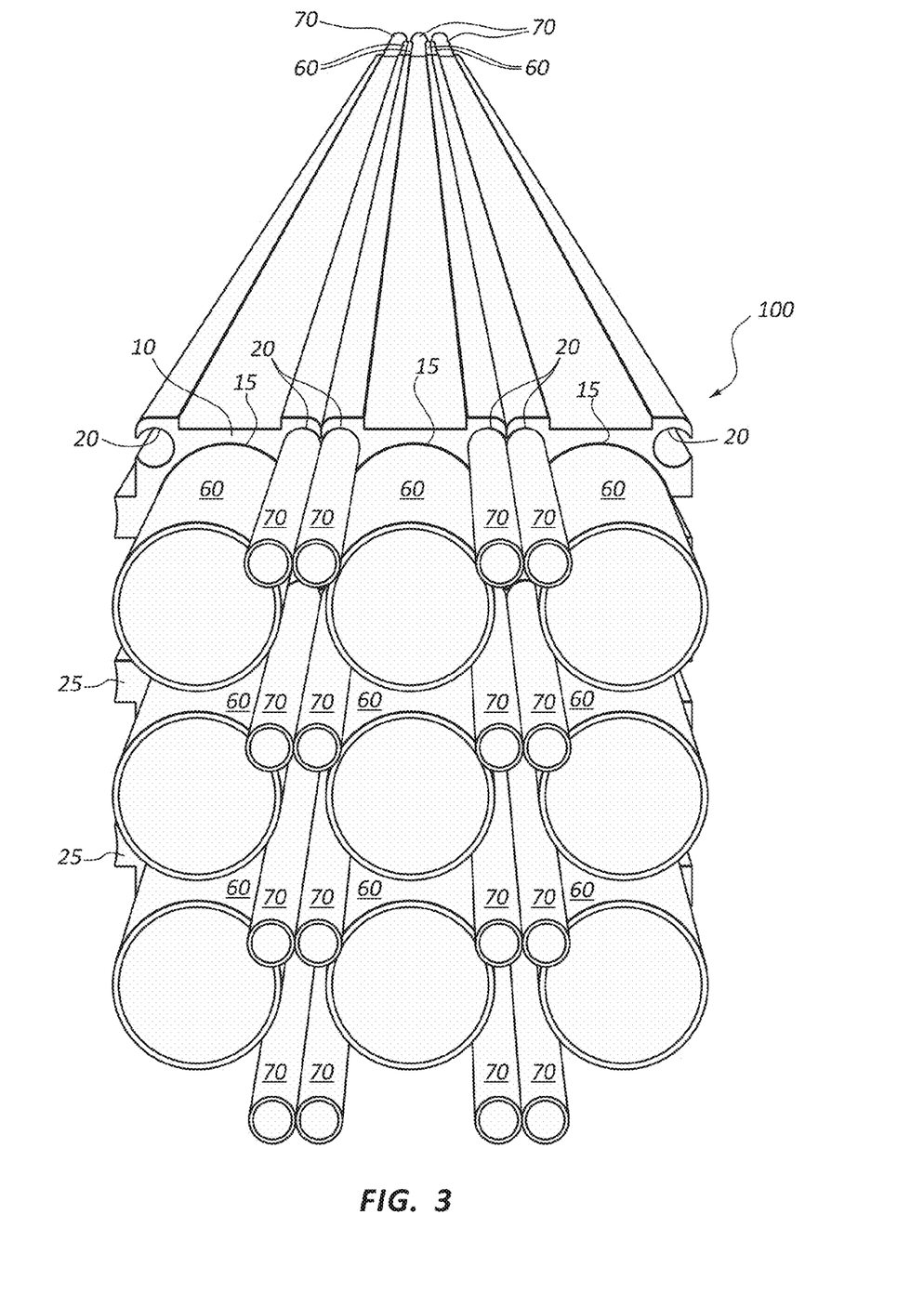
FIG. 3 shows the view of FIG. 2 in which some pipes have been added.

Referring now to FIG. 3, the perspective view of FIG. 2 is illustrated in which FT reactor tubes 60 have been placed within the apertures 15. As noted above, each aperture 15 is designed to receive a FT reactor tube 60. In the embodiment of FIG. 3, all of the apertures 15 have been filled with tubes 60. Those skilled in the art will appreciate that other embodiments may be designed/constructed in which some of the apertures 15 are empty (and do not have FT reactor tubes therein.). Likewise, FIG. 3 shows cooling tubes 70 that have been added to some of the cooling channels 20. As noted above, each cooling channel 20 is designed to receive a cooling tube 70. However, for purposes of clarity, only some of the cooling tubes 70 are illustrated. For example, the empty cooling channels 20 may be filled with cooling tubes 70 in some embodiments. Likewise, some of the cooling tubes 70 shown in FIG. 3 may be removed, if desired.

It should be noted that the cooling block 10, when used with one or more FT reactor tubes 60, makes up a compact FT processing unit 100. This FT processing unit 100 is relatively compact, and thus, would enable the transport of the FT unit 100 to remote locations and thus provide access to additional possibilities for input feed stocks to the system. The present FT unit 100 would reduce size, weight, and potentially manufacturing cost.

Figure 4:
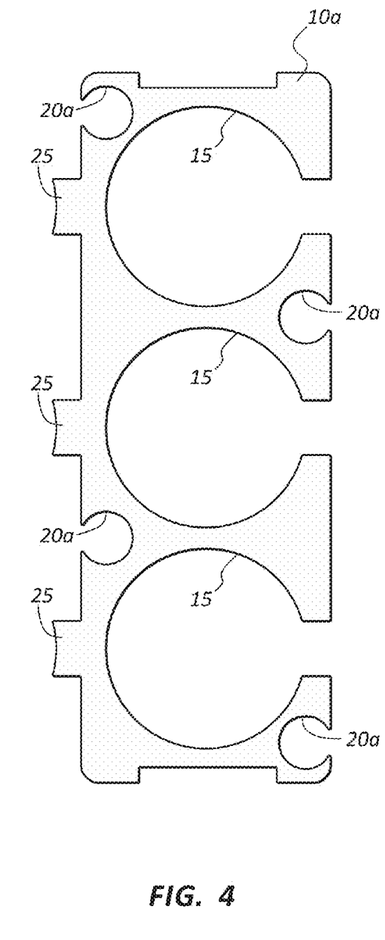
FIGS. 4 and 4a shows a plan drawings of other embodiments of a cooling block.
Figure 4A:
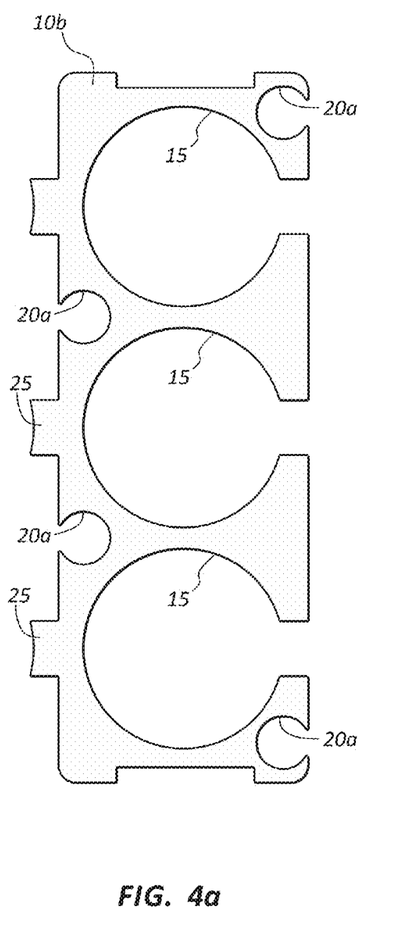

Referring now to FIG. 4 and FIG. 4a, further embodiments of a cooling blocks 10a, 10b are illustrated. Specifically, as shown in FIGS. 4 and 4a, the placement of the cooling channels 20a has been modified. (Those skilled in the art will appreciate that the shape, number and configuration of the cooling channels 20a may also be changed.) The channels may be re-positioned to be more symmetrical or asymmetrical, as desired. Further, the shape, size and position of the cooling channels 20a may be selected to produce a co-flow, counter-flow, serpentine, or cross-flow flow pattern, or any combination of flow patterns, as desired. Those skilled in the art will appreciate how to construct/shape the cooling channels 20a to achieve a desired flow pattern of the coolant fluid.

Figure 5A:
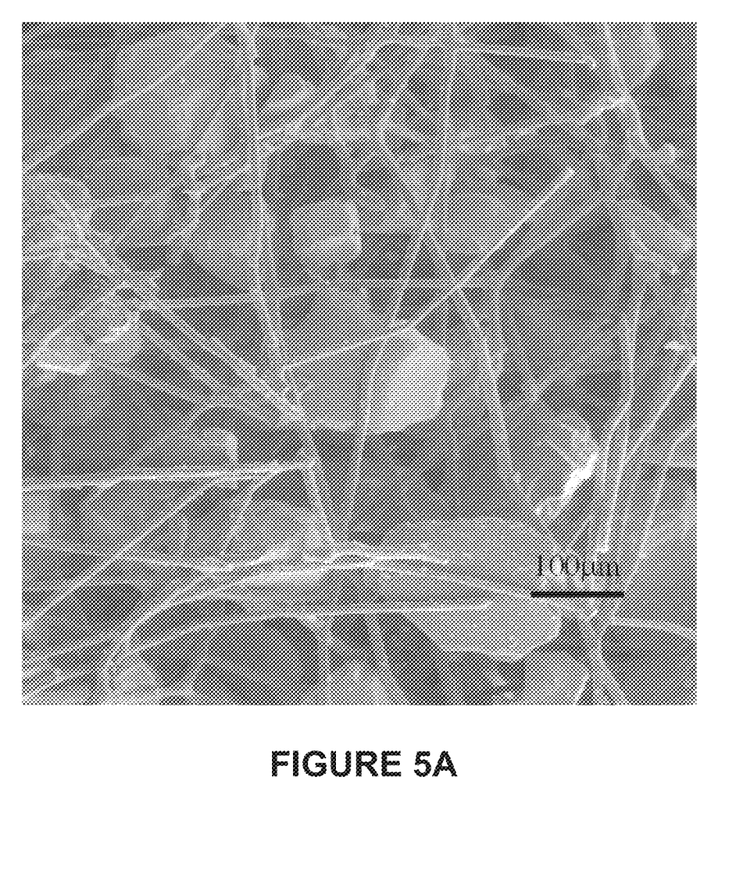
FIG. 5A is a photomicrograph of nano-particles of a catalyst in a micro-fibrous structure.
Figure 6:
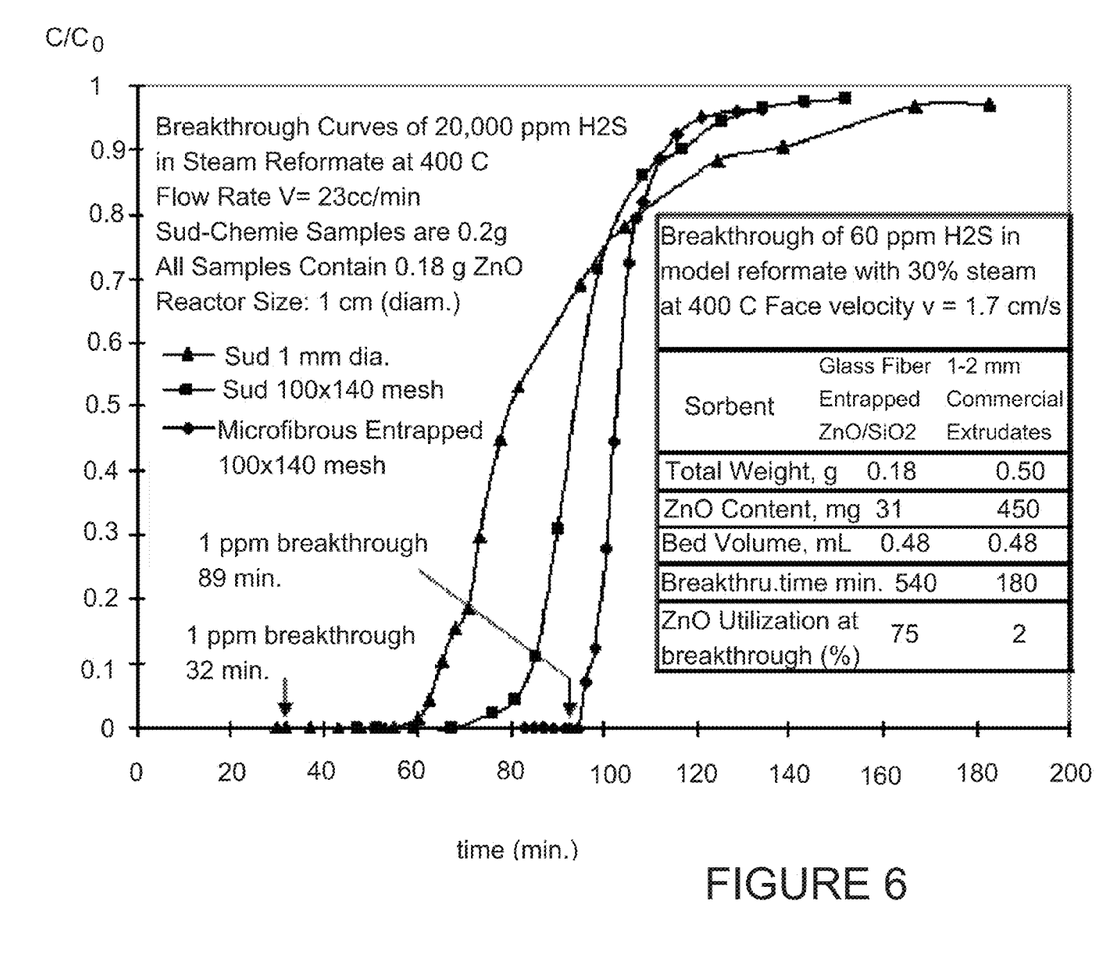
FIG. 6 is a graph showing when sulfur in the syngas will poison various types of catalysts, including a nano-dispersed catalyst in a micro-fibrous structure.

As will be appreciated by those skilled in the art, the FT reactor tube 60 is designed such that reactant carbon monoxide and hydrogen gas may be converted into water and a hydrocarbon. Of course, in order to conduct this reaction, a catalyst may be involved. The present embodiment of FT reactor tube 60 may use any type of catalyst/catalyst structure. However, one particular type of catalyst that has been found to be effective is an FT catalyst that has been dispersed within the tubular structures of the compact tube 60 using technology that provides a micro-fibrous substrate for dispersal of nano-sized FT catalyst. A photomicrograph of a typical micro-fibrous structure is shown in FIG. 5A. The use of this type of substrate could assist in solving many of the traditional problems with a fixed bed FT unit. The micro-fibrous structure breaks up flow and thus promotes a more even distribution of the synthesis gas through the FT synthesis tube. Further, a micro-fibrous structure is believed to provide increased activity by the better utilization of the supported structure (see data in FIG. 6 showing breakthrough extension using nano-sized zinc oxide for removal of sulfur from a gaseous stream). Proper selection of the micro-fibrous structure could also promote heat transfer (i.e., use of a metallic material for the removal of heat from the highly exothermic FT process and conveying it to the walls of the unit). Those skilled in the art will appreciate what materials may be used as the micro-fibrous material. Since excess heat promotes growth of undesirable light gaseous hydrocarbons, removal of heat has limited the use of fixed bed FT units.

Figure 5B:
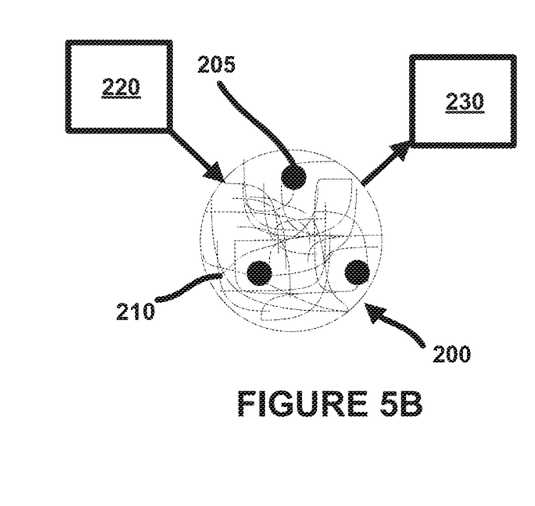
FIG. 5B is a schematic representation of the micro-graph of FIG. 5A.

FIG. 5B is a schematic representation of the photomicrograph of FIG. 5A. As shown in FIG. 5B, the catalyst 200 comprises the metallic catalyst 205 (which is a nano-particle) that is nano-dispersed micro-fibrous material 210. As shown in FIG. 5B, the nano-particle catalyst 205 are shown as circles, although those skilled in the art will appreciate that this representation is made for clarity and that other particle shapes may be used. The catalyst 200 (e.g., the nano-dispersed micro-fibrous material 210 and the nano-particle catalyst 205 are packed within the FT reactor tube (not shown in FIGS. 5A and 5B) and the syngas is allowed to pass through the tube, thereby causing an FT reaction to occur. Further, FIG. 5B shows that syngas 220 is added to the reactor tube and, while in the tube, an FT reaction occurs such that a hydrocarbon material 230 is produced.

The graph of FIG. 6 shows the much later breakthrough of the sulfur species when a microfiber support is used in a sulfur sorbent reactor. The clear implication is better mass transfer and catalyst effectiveness or reactant utilization factor resulting from the use of very small particles suspended by the microfibers. The proposed structure would allow longer use of a catalyst bed for a given length of tube in the FT unit or through the increased activity a shorter tube for a set time of use. Since the micro-fibrous structure would also form an easily removable catalyst bed, the time required for replacement of catalyst would be reduced. This would increase total availability of the unit.

Although some of the present embodiments involve the use of micro-fiber technology in the catalyst, those skilled in the art will appreciate that other embodiments may be constructed in which other types of catalysts, including conventional catalysts, are used with the cooling block 10.

Figure 7:
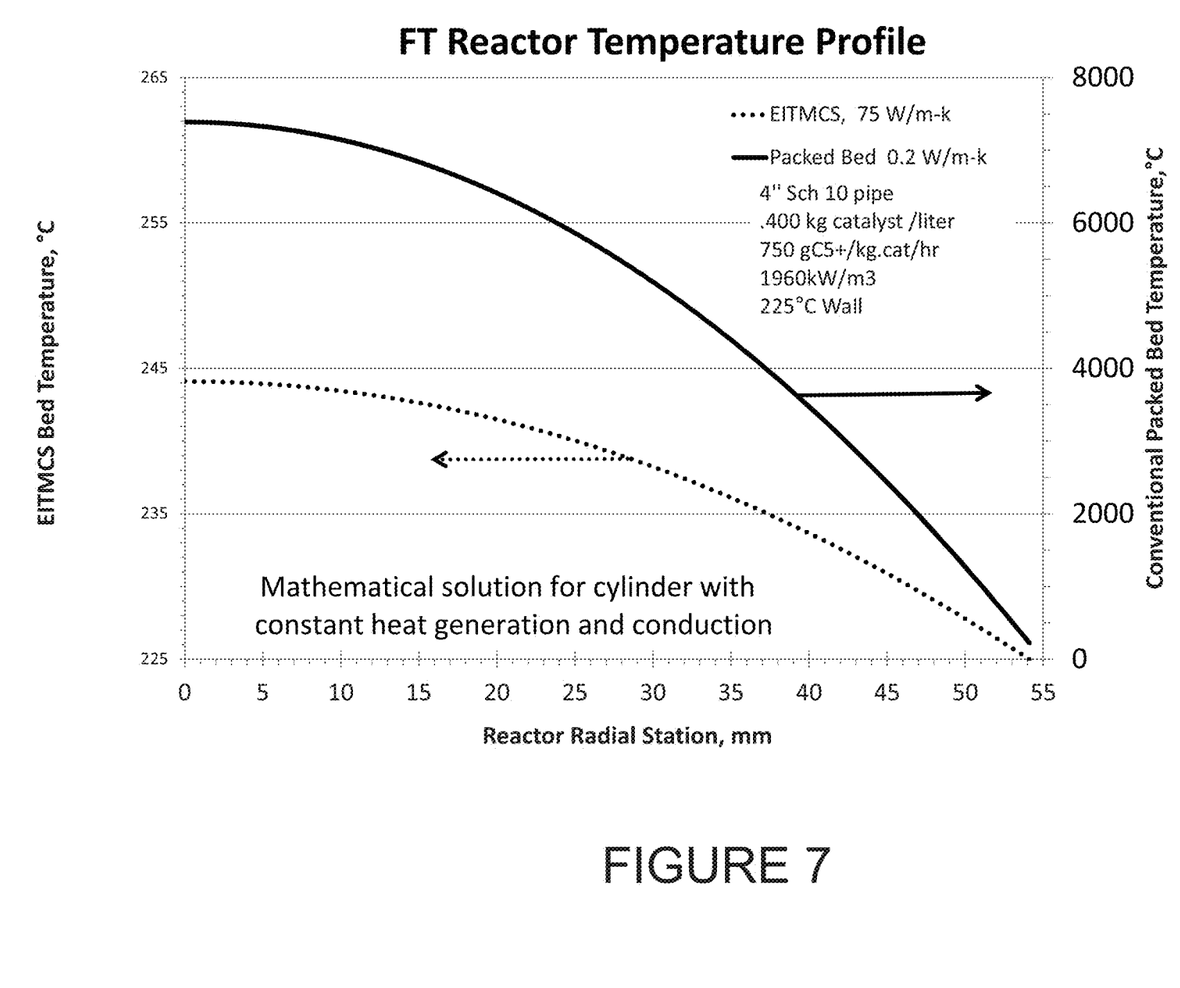
FIG. 7 is a graph showing the temperature profile in a cylinder with constant heat generation.
Figure 8:
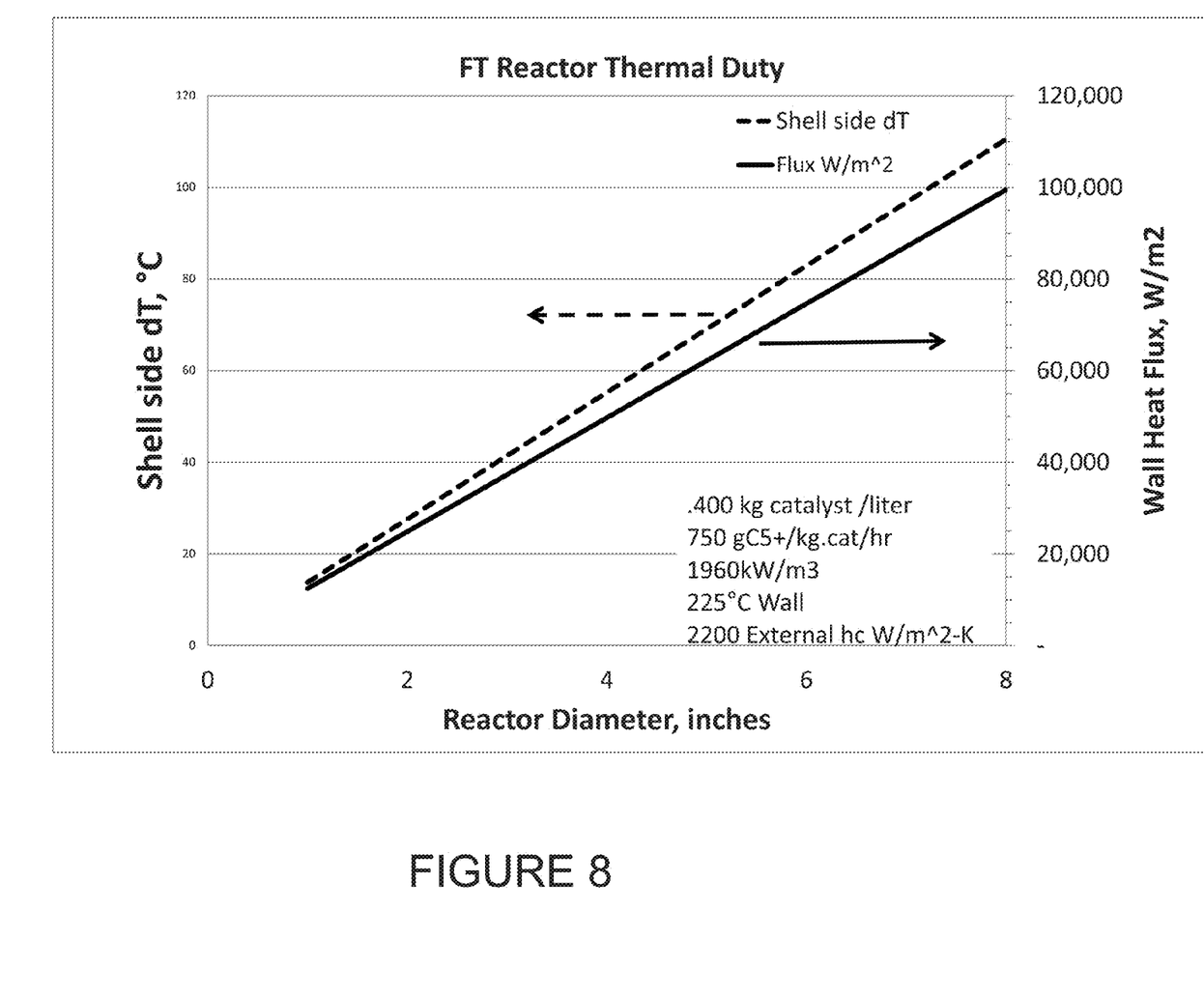
FIG. 8 is a graph of the diameter of the FT tube wall with respect to the desired number of barrels per day of FT product.
Figure 9:
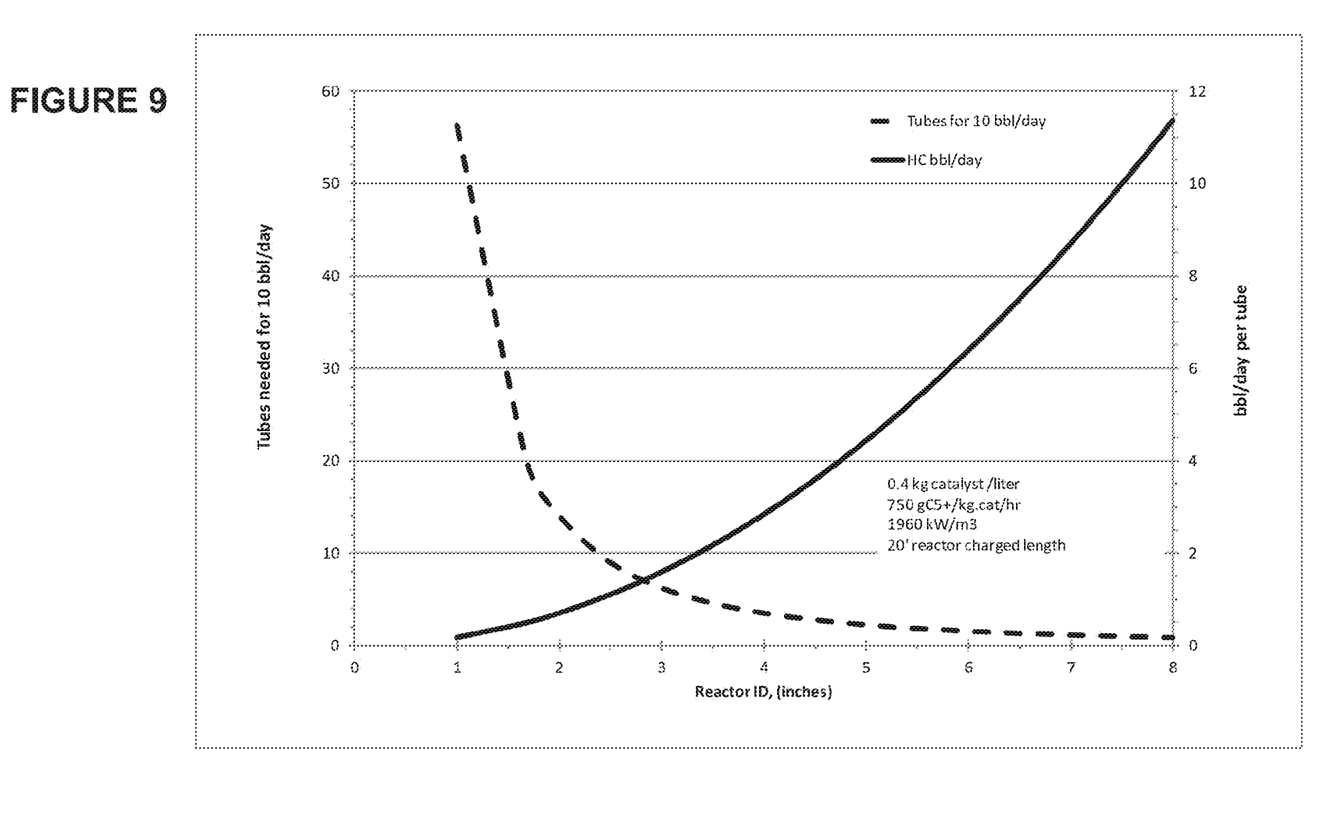
FIG. 9 is a graph of the FT reactor product as a function of the diameter of the FT tube.

The graphs shown in FIGS. 7-9 show the advantage of an enhanced internal thermal management catalyst structure ("EITMCS"), which in certain embodiments can be the insert and the MFEC (described below), either alone or in combination with each other. Specifically, these graphs show the advantages of the present embodiments in terms of temperature control, and the potential reactor size and productivity vs. reactor diameter. The graphs are based on reactor data and projected state of the art high activity catalyst.

As shown in FIG. 7, the expression for the temperature profile in a cylinder with constant heat generation is shown. At a given catalyst activity the heat generation rate $q'''$ is fixed. The effective bed conductivity k limits the maximum reactor tube diameter ($2*r_w$). A high effective bed conductivity allows the use of larger diameter reactors.

The Microfiber supported catalyst (which is sometimes called an "MFEC") can have an effective bed conductivity 50 times that of a conventional extrudate packed bed, allowing 7 times the reactor diameter for the same temperature difference. Alternatively, and/or additionally, embodiments of the present invention (including the use of the cooling block and the MFEC catalyst) could also incorporate an internal heat transfer fin or insert within the FT tube. This type of heat transfer fin/insert is described in U.S. Provisional Patent Application Ser. No. 61/600,501, filed Feb. 17, 2012 (which patent application is expressly incorporated herein by reference), may also be used to increase the effective bed thermal conductivity. In other words, the insert of the above-recited provisional patent application may be placed within the FT tube as a way of further dissipating heat from the interior of the tube.

The reactor tube must be capable of carrying off heat once heat has been conducted to the reactor tube wall. The graph of FIG. 8 shows the tube wall heat flux values vs. reactor size and the coolant $\Delta T$ assuming a typical value for a forced convection heat transfer coefficient hc. The present embodiments provide an improved means of supporting high reactor wall heat transfer while maintaining a very uniform temperature along the length of the reactor.

The reactor tube addresses heat removal at the wall, by a novel design with integrated primary and secondary bed temperature control. The graph of FIG. 9 shows the benefits associated with having a larger diameter reactor tube, in order to produce a desired number of bbl (barrels FT product) per day. As shown by the graph of FIG. 9, conventional FT reactors are limited to about 1" diameter for a less active catalyst to ⅝" or smaller diameter for a very active catalyst. However, the MFEC with the present embodiments, along with the heat transfer inserts as described in U.S. Provisional Patent Application Ser. No. 61/600,501 and that primary and secondary bed temperature control designs as described in U.S. Provisional Patent Application Ser. No. 61/601,134 allow the use of reactor tubes of up to 4" with the most active known catalyst or up to 10" with less active catalysts. This reduces the cost and complexity required for a given production rate.

EXAMPLE

Figure 10:
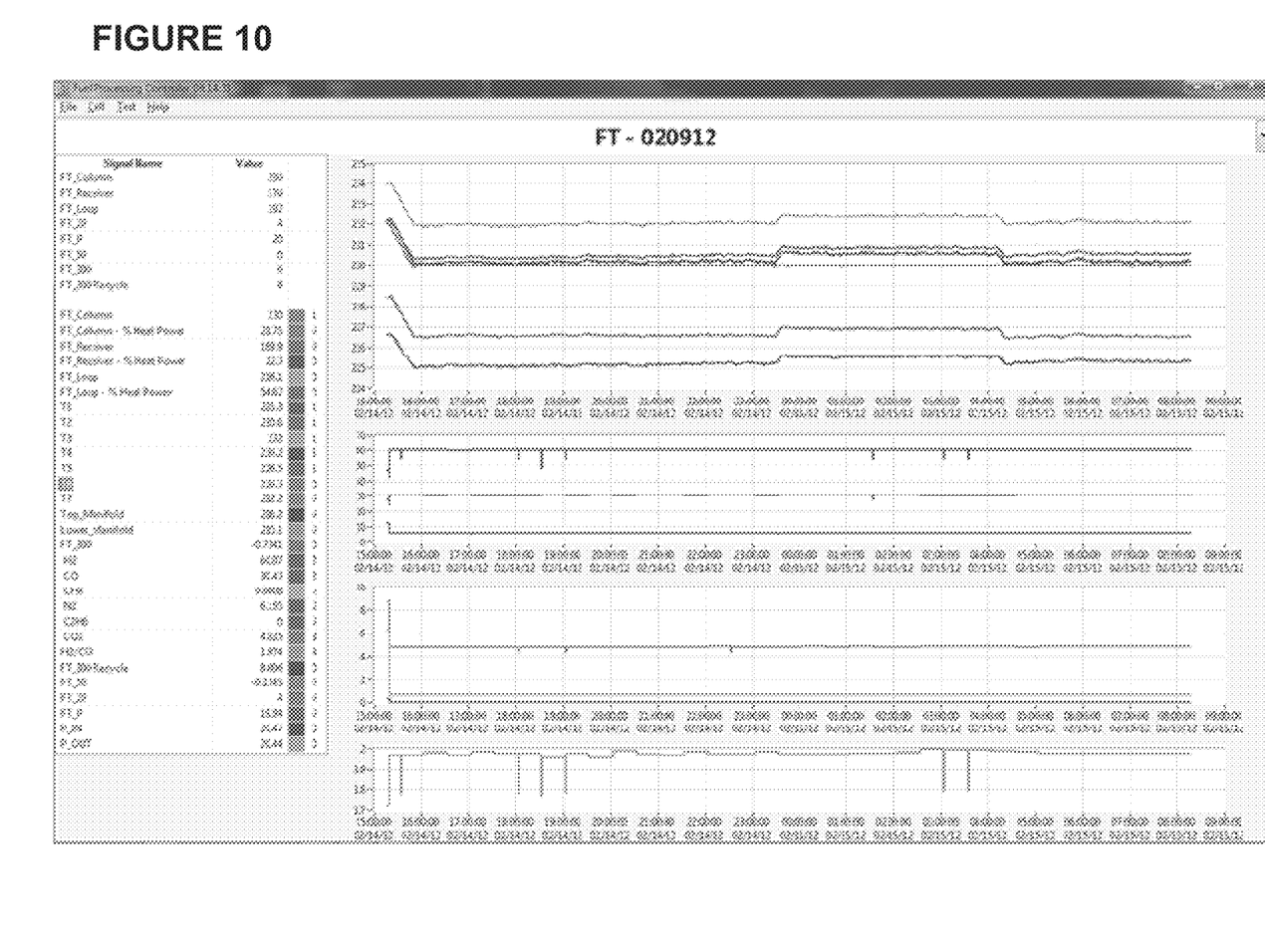
FIG. 10 is a graph of an exemplary data from an FT reactor that was constructed to include a nano-dispersed catalyst in a micro-fibrous structure.

FIG. 10 is a graph showing data from an FT reactor tube that was created using an MFEC catalyst. The following is an analysis of this data: Column 230° C. (control thermocouple (TC) embedded in aluminum extrusion) Top oil manifold (exit cooling oil temperature) 216.1° C.

T1-T7 is the reactor internal centerline temperature readings from top to bottom of the catalyst bed of the Fischer Tropsch (FT) reactor.
T1 225.2° C. (reactant inlet temperature)
T2 230.2° C. (top of bed temperature)
T3 232.0° C.
T4 230.3° C.
T5 226.6° C. (this is probably just below the bottom of the bed)
T6 220.5° C.
T7 213.3° C.
Bottom oil manifold is the entrance cooling oil temperature, which is about 215.1° C. (oil flows from bottom to top through a block about 15° C. hotter than the oil).

The uniform temperature in the reaction zone (T2-T5) shows the effectiveness of the modular reactor design in maintaining an uniform temperature. The bottom to top oil manifold temperatures (1° C. difference) show the good coupling (15° C. cooler than the reactor body [column at 230° C.]) and uniform heat sink they provide.

The advantage of the modular FT with microfiber is shown by the difference in temperature of T2-T5 (reaction zone centerline temperatures) vs. the external reactor module temperature (230° C.).

All the patent applications and patents listed herein are expressly incorporated herein by reference.

What is claimed is:

1. A cooling block comprising:
a set of modular cooling blocks, each block defining a plurality of longitudinal channels, the channels comprising:
an aperture channel sized to receive a Fischer Tropsch ("FT") reactor tube; and
a cooling channel aligned parallel to the aperture channel;
wherein each modular cooling block further comprises:
a female connector opening formed through a sidewall of the modular cooling block; and
a male connector extension formed on a sidewall of the modular cooling block to interlock with a corresponding female connector opening of a laterally adjacent and parallel modular cooling block.

2. The cooling block of claim 1, wherein the female connector opening forms an opening into at least one of the aperture channels, and a corresponding male connector extension of the laterally adjacent and parallel module cooling block closes off the female connector opening upon insertion into the female connector opening.

3. The cooling block of claim 2, wherein the opening of the female connector opening extends along the longitudinal length of the aperture channel.

4. The cooling block of claim 1, wherein each aperture channel is defined by a radius, and a distal surface of each male connector extension forms a concave arc defined by the same radius.

5. The cooling block of claim 4, wherein each male connector extension has an extension length to align the distal surface with an interior sidewall of a corresponding aperture channel upon insertion into the corresponding female connector opening.

6. The cooling block of claim 1, wherein each cooling channel extends along the longitudinal length of the modular cooling block, and each cooling channel has an opening which also extends along the longitudinal length of the modular cooling block.

7. The cooling block of claim 1, wherein the channels of each modular cooling block comprise a plurality of cooling channels, wherein the cooling channels are staggered on alternating sides of the aperture channels to dispose a single cooling channel between each set of four aperture channels.

8. The cooling block of claim 1, wherein the channels of each modular cooling block comprise a plurality of cooling channels, wherein the cooling channels are disposed in adjacent pairs of cooling channels between the aperture channels.

9. The cooling block of claim 1, wherein the aperture channel and the cooling channel are formed in a single integrated metal block.

10. The cooling block of claim 9, wherein the modular cooling block is formed of extruded aluminum.

11. The cooling block of claim 1, further comprising a FT reactor tube disposed in each aperture channel.

* * * * *